United States Patent [19]

Zoltobrocki

[11] 4,129,560

[45] Dec. 12, 1978

[54] PROCESS FOR THE PURIFICATION OF HIGH MOLECULAR WEIGHT PEPTIDES USING NON-IONIC DETERGENTS

[75] Inventor: Manfred Zoltobrocki, Frankfurt am Main, Fed. Rep. of Germany

[73] Assignee: Hoechst Aktiengesellschaft, Frankfurt am Main, Fed. Rep. of Germany

[21] Appl. No.: 810,979

[22] Filed: Jun. 29, 1977

[30] Foreign Application Priority Data

Jul. 1, 1976 [DE] Fed. Rep. of Germany ....... 2629568

[51] Int. Cl.² .................. C07C 103/52; C07G 7/00; C07G 15/00
[52] U.S. Cl. .................. 260/112 R; 260/112.5 R; 260/112.7
[58] Field of Search ............ 260/112 R, 112 B, 112.7, 260/112.5

[56] References Cited

U.S. PATENT DOCUMENTS

| | | | |
|---|---|---|---|
| 3,607,858 | 9/1971 | Querry | 260/112 B |
| 3,616,235 | 10/1971 | Schoepfel et al. | 260/112 R |
| 3,683,939 | 8/1972 | Johnsen et al. | 424/70 X |
| 3,907,676 | 9/1975 | Jorgensen | 260/112.7 |
| 3,983,008 | 9/1976 | Shinozaki et al. | 260/112 R |
| 4,076,800 | 2/1978 | Marsh et al. | 424/70 |

OTHER PUBLICATIONS

Proc. Natl. Acad. Sci. U.S.A., 1977, 74(2), pp. 529–532, Helenius et al.
Austral J. Biol. Sci. 13, 1960, pp. 393–400, Thompson et al.
Chem. Abstracts, vol. 77, 1972, 13057n, Jorgensen et al.

*Primary Examiner*—Howard E. Schain
*Attorney, Agent, or Firm*—Curtis, Morris & Safford

[57] ABSTRACT

Process for the purification of high molecular weight peptides, which have a tendency to associate, by ion exchanger chromatography in aqueous buffered solvents on acid or basic ion exchangers, which comprises dissolving non ionic detergents in the buffered solvents.

1 Claim, No Drawings

PROCESS FOR THE PURIFICATION OF HIGH MOLECULAR WEIGHT PEPTIDES USING NON-IONIC DETERGENTS

The present invention relates to a process for the purification of high molecular weight peptides which have a tendency to associate, by ion exchanger chromatography in aqueous buffered solvents on acidic or basic ion exchangers, which comprises dissolving non ionic detergents in the buffered solvents.

It is already known to separate peptides of the same or of similar molecular weight, which differ from one another by their basicity or acidity, on ion exchangers. This method, however, fails when the different peptides form complex compounds with one another which remain unchanged during the ion exchanger chromatography process. In order to bypass these difficulties dissociating conditions in the eluent have to be chosen. Up to now, for this purpose substances, such as for example urea or urea derivatives, have been dissolved in the buffers used for the elution, in high concentrations of from 5 M to 9 M or elution has been carried out in organic solvents miscible with water. Thus, for example, insulin was chromatographed on the ion exchanger Amberlite IRC 50 in phosphate buffer with 5–8 M of urea (cf. R. D. Cole, J. Biol. Chem. 235, 2294 (1960)). English patent 881,885 discloses the use of an organic solvent miscible with water, for example ethanol. Extreme pH values, which likewise have a dissociating action, cannot be applied because of the sensitivity of the peptides to these conditions. The processes known hitherto have various disadvantages. The isolation of the substances from urea-containing buffers, for example, is difficult and time-consuming; moreover, urea may contain impurities which act with peptides like insulin. When using ethanol as an organic solvent, the ion exchanger can be reused only with difficulty and moreover, the ion exchanger chromatography involves a high less of peptide, for example of insulin. Finally there is the danger of a denaturation of the high molecular weight peptides in organic solvents, which has been observed for insulin in 60% alcohol at pH 7.

It has now been found surprisingly that these difficulties can be bypassed by using non ionic detergents for the dissociation of the peptides.

In this case the reuse of the exchangers causes no difficulties. A denaturation of the peptides cannot be observed, their isolation is easy and is carried out by precipitation of the peptides with suitable precipitation agents and by possible subsequent crystallization. The yields are considerably higher than when using organic solvents as dissociating agent.

The process according to the invention is applicable to any high molecular weight peptides, of natural or synthetic origin which have a tendency to aggregate with themselves or with other similar compounds, for example insulins of all species, even human insulin, insulin analogous compounds, for example Des-Phe-B1-insulin, insulin derivatives, for example insulin-B-chain sulfonate, natural adrenocorticotropic hormone, growth hormone, glucagon, glycoproteid hormones of the anterior lobe of the pituitary gland, for example the Thyreoidea stimulating hormone, the luteotropic hormone, or the follicle stimulating hormone.

These compounds can be used both in a relatively impure form and in prepurified form (for example by gel chromatography). Even after multiple crystallization and after gel chromatography insulin is still contaminated by accompanying insulinoid substances of closely similar molecular weight. These substances differ from one another and from insulin in their state of charge at an adequately chosen pH and form complex compounds with insulin. Examples of such substances are: desamidoinsulins, arginine and diarginine insulin, insulin ethyl esters and others. They cannot be separated from insulin either by gel chromatography or by ion exchanger chromatography in eluents which have no dissociating action.

Suitable ion exchangers for the purification of the above mentioned peptides, especially of insulin and insulin analogous compounds, in the process of the invention are: Dowex 1, QAE-Sephadex, Biogel DM, DEAE-Sephadex, Amberlyst A 21 and A 29, DEAE-Sepharose CL 6B, DEAE-Cellulose, Dowex 50, CM-Sephadex, SP-Sephadex, CM-Sepharose CL 6B, cellulose phosphate, Biogel CM, Amberlite CG 50, CM-Cellulose, alginic acid and others. Basic ion exchangers on dextran basis such as DEAE-Sephadex or QAE-Sephadex are especially appropriate for the purification of insulin, insulin analogous compounds and insulin derivatives.

The ion exchange process is carried out in a buffered, aqueous solvent, wherein non-ionic detergents are dissolved.

Suitable non-ionic detergents are, by way of example: palmityl sorbitan polyethylene glycol ether, stearyl sorbitan polyethylene glycol ether, oleyl sorbitan polyethylene glycol ether, nonylphenol polyglycol ether (10–30 mols of ethylene oxide per mol of nonylphenol), polymerization products of propylene oxide and ethylene oxide (10–80% of ethylene oxide), fatty alcohol polyglycol ethers and polyglycol ethers of synthetic fatty alcohols.

Fatty alcohol polyglycol ethers are used especially suitably as they are highly efficient, easy to handle and show no adsorption of UV rays in the adsorption range of aromatic peptides and thus, the peptides can be identified more easily in the eluate. Moreover, the compounds are completely bio-degradable and they can, consequently, be used without any problems in view of the environmental protection.

The eluents always contain a buffer substance in order to control their pH. It is preferably operated with constant pH. When using a cation exchanger, the pH may be in the range of from 3 to 6.5 (in the case of acid peptides), preferably of from 4 to 6. When using an anion exchanger, the pH may be in the range of from 5.5 to 10, preferably of from 6 to 9.

Suitable buffer substances are known in the literature. The temperature during the ion exchanger chromatography process must be kept constant and is in the range of from 0° to 50° C., preferably of from 15° to 30° C. The solution employed for the elution contains besides the buffer substances and detergents an electrolyte, preferably a neutral salt such as NaCl, in concentrations of from 0.01 M to 0.5 M, preferably of from 0.05 M to 0.3 M. Alternatively, a gradient elution can be made by adding continuously an electrolyte-containing buffer to the elution buffer which has the same composition, but contains no electrolyte. The electrolyte buffer should be added in such a way that the concentration of the electrolyte employed increases in dependence on the elution volume. Linear dependence is preferred. The final electrolyte concentration is in the range of from 0.1 M to 1 M, preferably of from 0.3 M to 0.8 M.

The following examples illustrate the invention:

EXAMPLE 1

A buffer was prepared which had the following composition: 0.1 M of tris-(hydroxymethyl)-aminomethane 1% of Genapol$^R$ SE 150 (fatty alcohol polyglycol ether). The pH was adjusted to 7.0 with HCl.

To one part of the obtained buffer there were added 0.5 mol/l of NaCl. Thereafter 450 g of DEAE-Sephadex A 25 were soaked in the above buffer and the suspension was then fed to a column of 5 cm diameter and of 100 cm length. The column was equilibrated with the buffer.

5 g of insulin, which had been crystallized from citrate buffer, were dissolved in 74 ml of the above buffer (containing no NaCl). The final pH was 8.3. The clear solution was introduced into the column and eluted with the above buffer (pH 7.0) at 25° C. at a rate of 320 ml/h, while adjusting a linear NaCl gradient in a way to assure that the NaCl conentration in the eluate increased from 0 to 0.33 M, for a passage of 5.5 l of buffer. Fractions of 22 ml were collected. The extinction of UV rays in the eluate at 278 nm was measured continuously and traced. The central part of the insulin peak (in the range of from 0.1 M to 0.24 M of NaCl) (1540 ml) was collected and 70 ml of 1% ZnCl$_2$ solution were added thereto. The insulin precipitated in amorphous form was separated by centrifugation and thereafter crystallized in known manner from an aceton-containing citrate buffer.

The yield of pure insulin was 3.76 g (75.2%).

EXAMPLE 2

A buffer was prepared which had the following composition:
0.1 M of tris-(hydroxymethyl)-aminomethane
0.12 M of NaCl
1% of Genapol$^R$ ZDM 110 (polyglycol ether of straight chain, synthetic fatty alcohols (average molecular weight 190) and
11 mols of ethylene oxide/mol of fatty alcohol. The pH was adjusted to 7.0 with HCl.

13 g of QAE-Sephadex A 25 were soaked in the above buffer and the supension was then fed to a column of 1.5 cm diameter and of 30 cm length. The column was equilibrated with the buffer. 300 mg of insulin which, after crystallization, had been substantially freed from high molecular weight constituents in known manner by gel chromatography on Sephadex G 50, were dissolved in 15 ml of the above buffer (final pH 8.2). The clear solution was fed to the column and eluted with the above buffer (pH 7) at 25° C. at a rate of 48 ml/h. Fractions of 7 ml were collected. The extinction of UV rays in the eluate at 278 nm was measured continuously and traced. The central part of the insulin peak (620 ml) was collected and 28 ml of 1% ZnCl$_2$ solution were added thereto. The insulin precipitated in amorphous form was separated by centrifugation and crystallized in known manner from an acetone containing citrate buffer.

The yield of pure insulin was 185 mg /61.6%).

EXAMPLE 3

A buffer was prepared which had the following composition:
0.1 of tris-(hydroxymethyl)-aminoethane,
2% of Genapol$^R$ SE 150 (refer to Example 1)
The pH of the buffer was adjusted to 7.0 with HCl.

Parts of this buffer were mixed with 0.05 mol/l, 0.1 mol/l, 0.2 mol/l and 0.3 mol/l of NaCl, respectively.

450 g of DEAE-Sephadex A 25 were soaked in the above buffer containing 0.05 M of NaCl and the suspension obtained was introduced into a column of 5 cm diameter and of 100 cm length. The column was equilibrated with the buffer.

5 g of insulin (refer to Example 2) were dissolved in 100 ml of the above buffer (containing 0.05 M of NaCl) (final pH 8.4), introduced into the column and eluted at 25° C. at a rate of 290 ml/h. Fractions of 28 ml were collected. when 1.82 l of the buffer containing 0.05 M of Nacl had passed, 4,76 l of buffer containing 0.1 M of NaCl, 2.24 l of buffer containing 0.2 M of NaCl and finally 5.3 l of buffer containing 0.3 M of NaCl were fed to the column subsequently. The extinction of UV rays of the eluate was measured continuously and traced.

The main quantity of the insulin was eluted after addition of the buffer which contained 0.3 M of NaCl. The central part of the insulin peak was collected (820 ml) and mixed with 37 ml of 1% of ZnCl$_2$ solution. The amorphous precipitate was separated by centrifugation and the insulin was crystallized in known manner from an acetone-containing citrate buffer.

The yield of pure insulin was 2.84 g (56.8%).

EXAMPLE 4

A buffer was prepared from
0.1 M of tris-(hydroxymethyl)-aminomethane
5% of Genapol$^R$ SE 100 (fatty alcohol polyglycol ether).

The pH was adjusted to 7.0 with HCl.

A part of the buffer obtained was mixed with 0.5 mol/l of NaCl.

13 g of DEAE-Sephadex A 25 were soaked in the above buffer (containing no NaCl) and the suspension was fed to a column of 1.5 cm diameter and of 30 cm length. The column was equilibrated with the buffer. 300 mg of insulin (refer to Example 2) were dissolved in 15 ml of the above buffer (containing no NaCl) (final pH 8.3). The clear solution was introduced into the column and eluted at 25° C. at a rate of 48 ml/h, while applying a lineary NaCl gradient in a way to assure that the NaCl concentration in the eluate increased from 0 to 0.5 M after the passage of 500 ml of buffer. Fractions of 7 ml were collected. The extinction of UV rays in the eluate at 278 nm was measured continuously and traced. The central part of the insulin peak (in the range of from 0.09 M to 0.22 M of NaCl) (100 ml) was collected and 4.6 ml of 1% ZnCl$_2$ solution were added thereto. The insulin precipitated as amorphous substance was separated by centrifugation and thereafter crystallized in known manner from an acetone-containing citrate buffer.

The yield of pure insulin was 160 mg (53.3%).

EXAMPLE 5

The example was carried out as Example 4, with the exception that 1% of Arkopal$^R$N 100 (nonylphenol polyglycol ether with 10 mols of ethylene oxide/mol of nonylphenol) was used additionally as a detergent.

The continuous UV measuring had to be performed as differential measuring because of the individual absorption of Arkopal N 100. The yield of pure insulin was 214 mg (71.3%).

EXAMPLE 6

The example was carried out as Example 4, except that 2% of Arkopal$^R$ N 300 (nonylphenol polyglycol ether with 30 mols of ethylene oxide/mol of nonylphenol) was used as detergent and QAE-Sephadex A 25 as ion exchanger.

The yield of pure insulin was 156 mg (52%).

The continuous UV measuring had to be performed as differential measuring because of the individual absorption of Arkopal N 300.

The detergents used in the Examples are trade products of HOECHST AG.

The ion exchangers used in the examples are trade products of Pharmacia Fine Chemicals.

What is claimed is:

1. A method for purifying a high molecular weight peptide selected from the group consisting of insulins, insulin analogues, insulin derivatives, natural adrenocorticotropic hormone, growth hormone, glucagon, and glycoproteid hormones of the anterior lobe of the pituitary gland, which peptides have a tendency to associate, which method comprises subjecting a buffered solution of said peptide to ion exchange chromatography on an acidic or basic ion exchanger, said buffered solution additionally comprising a non-ionic detergent.

* * * * *